United States Patent
Hyde-DeRuyscher et al.

(10) Patent No.: US 10,160,796 B2
(45) Date of Patent: Dec. 25, 2018

(54) MAST CELL STABILIZERS FOR TREATMENT OF HYPERCYTOKINEMIA AND VIRAL INFECTION

(71) Applicant: Emergo Therapeutics, Inc., Chapel Hill, NC (US)

(72) Inventors: Robin Parish Hyde-DeRuyscher, Chapel Hill, NC (US); Nancy Harlan Hyde-DeRuyscher, Chapel Hill, NC (US); Elicia Kristine Hyde-DeRuyscher, Chapel Hill, NC (US)

(73) Assignee: Emergo Therapeutics, Inc., Chapel Hill, NC (US)

( * ) Notice: Subject to any disclaimer, the term of this patent is extended or adjusted under 35 U.S.C. 154(b) by 0 days.

(21) Appl. No.: 15/816,461

(22) Filed: Nov. 17, 2017

(65) Prior Publication Data

US 2018/0072796 A1    Mar. 15, 2018

Related U.S. Application Data

(62) Division of application No. 15/697,835, filed on Sep. 7, 2017.

(60) Provisional application No. 62/385,021, filed on Sep. 8, 2016.

(51) Int. Cl.
| A61K 31/00 | (2006.01) |
| C07K 16/10 | (2006.01) |
| C07K 14/52 | (2006.01) |
| A61K 39/42 | (2006.01) |
| A61K 38/17 | (2006.01) |
| A61K 45/06 | (2006.01) |
| A61K 39/00 | (2006.01) |

(52) U.S. Cl.
CPC ...... *C07K 16/1018* (2013.01); *A61K 38/1709* (2013.01); *A61K 39/42* (2013.01); *C07K 14/52* (2013.01); *A61K 2039/505* (2013.01); *C07K 2317/732* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,207,683 | B1 | 3/2001 | Aberg et al. | |
| 6,207,684 | B1 | 3/2001 | Aberg | |
| 7,226,934 | B1 | 6/2007 | Aberg et al. | |
| 8,557,846 | B1 | 10/2013 | Aberg et al. | |
| 9,138,431 | B2 | 9/2015 | Aberg et al. | |
| 9,333,199 | B2 * | 5/2016 | Aberg | A61K 31/4535 |
| 9,345,697 | B2 | 5/2016 | Aberg et al. | |
| 2003/0118670 | A1 | 6/2003 | Smith | |
| 2005/0049262 | A1 | 3/2005 | Klein et al. | |
| 2006/0084695 | A1 | 4/2006 | Griffin et al. | |
| 2008/0025976 | A1 | 1/2008 | Le et al. | |
| 2008/0085922 | A1 | 4/2008 | Raja et al. | |
| 2009/0169546 | A1 | 7/2009 | Wu et al. | |
| 2010/0105734 | A1 | 4/2010 | Aberg et al. | |
| 2010/0130550 | A1 | 5/2010 | Aberg et al. | |
| 2010/0166804 | A1 | 7/2010 | Penn | |
| 2012/0058984 | A1 | 3/2012 | Alder et al. | |
| 2014/0113936 | A1 | 4/2014 | Aberg et al. | |
| 2014/0120121 | A1 | 5/2014 | Aberg et al. | |
| 2014/0205562 | A1 | 7/2014 | Wu et al. | |
| 2014/0341913 | A1 | 11/2014 | Tripp | |
| 2015/0272941 | A1 | 10/2015 | Aberg et al. | |
| 2016/0046730 | A1 | 2/2016 | Ghayur et al. | |
| 2016/0193143 | A1 | 7/2016 | Aberg et al. | |
| 2016/0228426 | A1 | 8/2016 | Aberg et al. | |

FOREIGN PATENT DOCUMENTS

| CA | 2283663 A1 | 10/1998 |
| WO | 9835677 A1 | 8/1998 |
| WO | 2009088570 A1 | 7/2009 |
| WO | 2009142772 A2 | 11/2009 |
| WO | WO 2010/107525 A1 | 9/2010 |
| WO | 2011068786 A2 | 6/2011 |
| WO | 2014066212 A1 | 5/2014 |
| WO | 2014070696 A2 | 5/2014 |
| WO | 2016130958 A1 | 8/2016 |
| WO | 2017035418 A1 | 3/2017 |

OTHER PUBLICATIONS

Graham et al. "Mast cells and influenza A virus: association with allergic responses and beyond", Frontiers in Immunology 5:1-12 (2015).

Han et al. "The therapeutic effects of sodium cromoglycate against influenza A virus H5N1 in mice", Influenza and Other Respiratory Viruses 10(1):57-66 (2016).

Hu et al. "Mast Cell-Induced Lung injury in Mice Infected with H5N1 Influenza Virus", Journal of Virology 86 (6):3347-3358 (2012).

Notification of Transmittal of the International Search Report and the Written Opinion of the International Searching Authority, or the Declaration corresponding to International Application No. PCT/US2017/050409 dated Dec. 14, 2017.

U.S. Appl. No. 15/697,835, filed Sep. 7, 2017; Office Action dated Dec. 15, 2017.

Gwathmey et al. "Neurologic indications for therapeutic plasma exchange: an update.", *J Clin Apher.* 26(5):261-8 (2011) Abstract Only.

(Continued)

*Primary Examiner* — Nicole Kinsey White
(74) *Attorney, Agent, or Firm* — Myers Bigel, P.A.

(57) ABSTRACT

The present invention relates to methods for treating hypercytokinemia and viral infections associated with hypercytokinemia using a mast cell stabilizing compound, optionally in combination with an antiviral agent. The invention further relates to compositions and dosage forms comprising mast cell stabilizing agents, optionally with an antiviral agent.

11 Claims, 1 Drawing Sheet

(56) References Cited

OTHER PUBLICATIONS

Liu et al. "The cytokine storm of severe influenza and development of immunomodulatory therapy", *Cellular & Molecular Immunology* 13;3-10 (2016).

Negro-Alvarez et al. "Antiallergic properties of antihistamines,", *Allergol Immunopathol (Madr.)* 24(4):177-83 (1996) Abstract Only.

Nishibori et al. "[Regulation of cytokine production by histamine through H2-receptor stimulation].", *Nihon Yakurigaku Zasshi* 118(1):29-35 (2001) Abstract Only.

O'Brien et al. "Oseltamivir for Treatment of Influenza in Healthy Adults: Pooled Trial Evidence and Cost-Effectiveness Model for Canada", *Value in Health* 6(2):116-125 (2003).

Patel et al. "Use of therapeutic plasma exchange as a rescue therapy in 2009 pH1N1 influenza—An associated respiratory failure and hemodynamic shock", *Pediatric Critical Care Medicine* 12(2):1-3 (2011).

St. John "Influence of Mast Cells on Dengue Protective Immunity and Immune Pathology", *PLOS Pathogens* 9(12):e1003783 (2013).

Teljaro et al. "Mapping the innate signaling cascade essential for cytokine storm during influenza virus infection", *PNAS* 111(10):3799-3804 (2014).

Yang et al. "The role of mast cells in ischemia and reperfusion injury", *Inflamm. Res.* 63:899-905 (2014).

\* cited by examiner

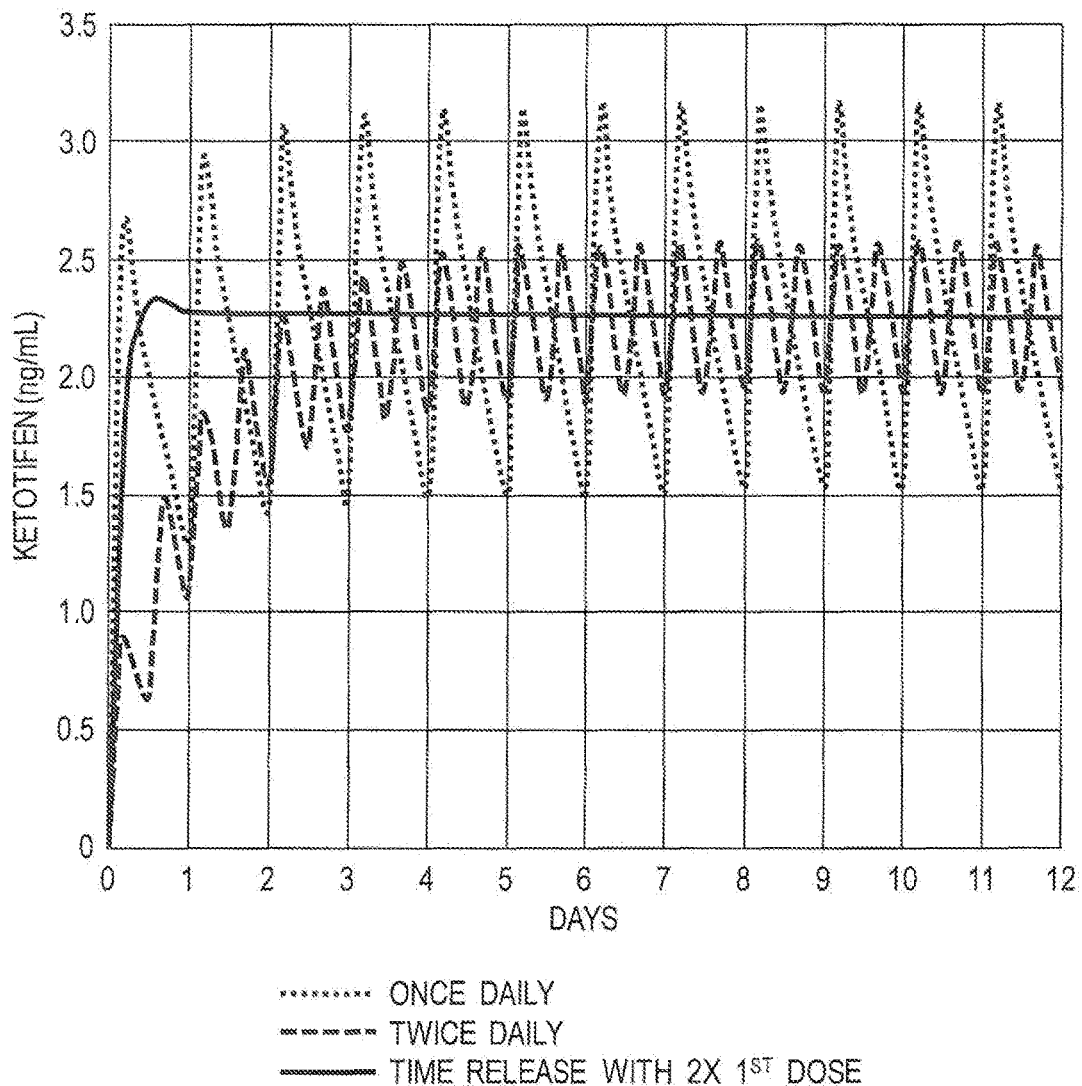

MAST CELL STABILIZERS FOR TREATMENT OF HYPERCYTOKINEMIA AND VIRAL INFECTION

STATEMENT OF PRIORITY

This application is a divisional of and claims priority to U.S. patent application Ser. No. 15/697,835, filed Sep. 7, 2017 which claims the benefit of U.S. Provisional Application Ser. No. 62/385,021, filed Sep. 8, 2016, the entire contents of which are incorporated by reference herein.

FIELD OF THE INVENTION

The present invention relates to methods for treating hypercytokinemia and viral infections and other disorders associated with hypercytokinemia using a mast cell stabilizing compound, optionally in combination with an antiviral agent or other therapeutic agent. The invention further relates to compositions and dosage forms comprising mast cell stabilizing agents, optionally with an antiviral agent or other therapeutic agent.

BACKGROUND OF THE INVENTION

Mast cells are a unique hematopoietic cell that is resident only in tissue and not in the blood stream. They are sentinels, constantly on the lookout for invading organisms, toxic molecules and tissue damage. When mast cells encounter such pathogens or damage, they release a flood of mediators; these mediators are a mix of small molecule effectors (such as histamine), proteases, lipid-derived signaling molecules (prostaglandins) and cytokines. The process of releasing these mediators is generically termed "degranulation."

The release of mediators via degranulation results in the recruitment of a wide variety of immune cells to the site of mediator release to fight the offending intruder. This process also induces localized inflammation to restrict the movement of any infection or toxin. A controlled inflammatory response to foreign bodies enables the body to prevent the spread of toxins to neighboring tissues, limiting damage to one area and is desirable. Once the toxin has been neutralized, the normal course is for the body to begin an active resolution of inflammation response (ROI). This results in an egress of recruited immune cells from the injured tissue, tissue remodeling, a reduction in swelling and finally complete healing.

In some cases, this normal course of a proportional inflammatory response, followed by resolution is not followed. This can result in either a chronic state of inflammation or an overly robust mediator response that is out of proportion to the invading event. The latter scenario has been termed a "cytokine storm" or hypercytokinemia. An extremely high level of inflammatory cytokines and mediators that is not resolved is harmful to the host and can result in death, especially if the run-away response occurs in the lungs. The most damaging aspects and symptoms of many diseases are a direct result of hypercytokinemia, as opposed to damage from the original disease.

Current treatments for conditions that induce hypercytokinemia do not generally do anything to ameliorate the ongoing production of inflammatory mediators that perpetuate this condition. These conditions are usually treated by interventions that target the pathogen inducing the response or by using antagonists to one specific inflammatory mediator. While it is critical for the pathogens to be neutralized, in most diseases that induce hypercytokinemia, the problem is not the pathogen, but rather the body's overly robust response to the pathogen by a dozen or more inflammatory mediators.

Nevertheless, down regulating the immune system is not enough on its own to treat these conditions. In fact, there is evidence in some cases suggesting that treating patients with corticosteroids to reduce inflammation increases mortality. Corticosteroids are very powerful down regulators of the innate and adaptive immune system. "Turning off" all aspects of the immune response during an infection does not allow the clearance of the pathogen. Thus, a balance must be struck between an overly robust immune response and too little of a response.

Influenza viruses are a related series of viruses in the Orthomyxoviridae family. Three types have been described (Types A, B or C) and all are negative-sense, segmented, single stranded RNA viruses. Types A and B are medically relevant to human health with type A being the cause of more severe disease. Type A viruses are normally found in wild birds and only rarely cause disease in their host. Influenza A subtypes routinely cause waves of human influenza disease across the globe with far reaching health and economic consequences. In the US, approximately 30,000 people die each year from flu or complications resulting from influenza infection. The estimates on economic impact in the US are greater than $80 billion/year in direct medical costs and lost work. Influenza usually infects humans through the respiratory tract, although there are also reports that infection can occur through the eyes.

Influenza induces a rapid cytokine response in humans, usually detectable within hours of infection. An important point to note is that the severity of each case of flu is directly correlated with the levels of induced cytokines. This is well known to those in the field and has been documented across many different strains of influenza. What is particularly striking about influenza induced disease is that severity is dependent on the viral strain and the individual. For instance, most yearly cases of influenza are caused by the H1N1 strain. While many people are infected, the severity of the disease ranges from no symptoms to death. In a normal H1N1 seasonal flu season in the US, about 20% of the population are sickened (60 million people), 200,000 of those are hospitalized and about 30,000 people die each year (about 0.05% mortality). In outbreaks involving highly pathogenic strains of the virus (H5N1 for instance) 30% to 60% of the cases are fatal. While this indicates that the virus is the main cause of severity, the reason that people exhibit more severe or fatal disease is the same with either strain: the dangerously ill people have extremely high levels of cytokines, regardless of viral strain. Thus, the problem is not really the virus itself, but rather the body's response to the virus. In more virulent strains, a larger proportion of people will experience hypercytokinemia. However, this hypercytokinemia is no different than it is in the small proportion of people that experience the same symptoms from a less virulent strain.

Mast cell stabilizers such as ketotifen and cromolyn (sodium cromoglycate) have been shown to inhibit mast cell degranulation and the resulting release of mediators such as histamine, tumor necrosis factor (TNF)-α, prostaglandins, leukotrienes, interleukins and other cytokines. These effects may not be limited to mast cells and might have a broader effect of reducing inflammatory cytokine release in multiple cell types. These compounds, however, do not impact the adaptive immune system and allow antibody based clearance of foreign bodies from the body to continue essentially as normal. Both of these compounds are used to treat chronic conditions. Cromolyn was discovered and used as an inhaled treatment for asthma. Ketotifen was discovered as an H1 antihistamine and is used extensively in eye drop formulations to treat eye inflammation. It was also developed as an oral treatment for asthma, although this seems to take several weeks for it to have significant impact on chronic asthma. Ketotifen and to a lesser extent cromolyn have been shown to increase survival of mice in a model system of influenza infection (Hu et al., Mast Cell-Induced Lung Injury in Mice Infected with H5N1 Influenza Virus, *J. Virol.* 86(6):3347 (2012); Han et al., The therapeutic effects of sodium cromoglycate against influenza A virus H5N1 in mice, *Influenza and Other Respiratory Viruses* 10(1):57 (2016)). In the case of ketotifen, it was combined with oseltamivir and the impact on survival was increased when the compounds were combined.

The present invention overcomes shortcomings in the art by providing compositions and methods for treating hypercytokinemia and disorders associated therewith.

SUMMARY OF THE INVENTION

The present invention relates to the development of treatments to down regulate hypercytokinemia in order to intervene successfully in cases of cytokine storm. The present invention provides a more effective way to aid the body in balancing inhibition of an overly robust immune response and providing too little of a response to provide a treatment that allows both problems to be addressed: the initial condition that the body is reacting to (i.e., infection) and the resulting hypercytokinemia. This can be accomplished with a treatment regime that down regulates the innate immune system and allows the adaptive immune system to remove the offending pathogen. Alternatively, a treatment that down regulates the innate immune system can be combined with a treatment to help clear the intruding particles (for example, an anti-viral compound).

Accordingly, as one aspect, the invention provides a method of treating, ameliorating, or preventing hypercytokinemia in a subject in need thereof, comprising administering to the subject a therapeutically effective or prevention effective amount of a mast cell stabilizing compound, thereby treating, ameliorating, or preventing the hypercytokinemia. In some embodiments, the method further comprises administering to the subject an additional therapeutic agent, e.g., an antiviral agent.

The invention further relates to a method of treating, ameliorating, or preventing a viral infection associated with hypercytokinemia in a subject in need thereof, comprising administering to the subject a therapeutically effective or prevention effective amount of a mast cell stabilizing compound, thereby treating, ameliorating, or preventing the viral infection. In some embodiments, the method further comprises administering to the subject an additional therapeutic agent, e.g., an antiviral agent.

The invention further relates to a method of treating, ameliorating, or preventing a disorder associated with hypercytokinemia in a subject in need thereof, comprising administering to the subject a therapeutically effective or prevention effective amount of a mast cell stabilizing compound, thereby treating, ameliorating, or preventing the disorder. In some embodiments, the method further comprises administering to the subject an additional therapeutic agent, e.g., an antiviral agent.

The invention further relates to a method of treating, ameliorating, or preventing a fever in a subject in need thereof, comprising administering to the subject a therapeutically effective or prevention effective amount of a mast cell stabilizing compound, thereby treating, ameliorating, or preventing the fever. In some embodiments, the method further comprises administering to the subject an additional therapeutic agent, e.g., an antipyretic agent.

The invention also relates to a pharmaceutical composition comprising norketotifen and a pharmaceutically acceptable carrier, and optionally an additional therapeutic agent.

The invention additionally relates to a pharmaceutical composition comprising ketotifen, an additional therapeutic agent, and a pharmaceutically acceptable carrier.

The invention further relates to dosage forms comprising the pharmaceutical compositions of the invention.

The present invention is explained in greater detail in the drawings herein and the specification set forth below.

BRIEF DESCRIPTION OF THE DRAWINGS

FIG. 1 shows predicted serum levels of ketotifen in a subject during several different dosing regimens.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the time period of symptoms is less than what would occur in the absence of the present invention.

A "treatment effective" or "therapeutically effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, the term "hypercytokinemia," also known as a "cytokine storm" or "cytokine cascade," refers to an immune reaction consisting of a positive feedback loop between cytokines and mediator secreting cells resulting in highly elevated levels of various cytokines. During hypercytokinemia, the serum and/or organ levels of one or more cytokine may be elevated, e.g., at least 5-fold higher than the level observed in a healthy subject or in a healthy population, e.g., at least 10-fold or 100-fold higher. Symptoms of hypercytokinemia may include high fever, swelling and redness, extreme fatigue, and nausea.

A "disorder associated with hypercytokinemia" refers to any disorder that has hypercytokinemia as one of its symptoms or side effects during at least one stage of the disorder.

A "viral infection associated with hypercytokinemia" refers to any viral infection that has hypercytokinemia as one of its symptoms or side effects during at least one stage of the infection.

"Influenza," as used herein, is defined as an illness associated with a positive influenza diagnostic test.

"Influenza-like illness," as used herein, is defined as the symptoms of fever (temperature of 37.8° C. or higher), and a cough and/or a sore throat without a known cause.

"Systemic inflammatory response syndrome (SIRS)" or "sepsis" is defined by the presence of two or more of the following clinical findings: (a) body temperature greater than 38° C. or 36° C.; (b) heart rate greater than 90 per minute; (c) respiratory rate greater than 20 per minute or $PACO_2$ less than 32 mmHg; (d) white blood cell count greater than 12,000 cell/L or less than 4,000 cells/L, or greater than 10% immature (band) forms.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's Pharmaceutical Science; $21^{st}$ ed. 2005). Exemplary pharmaceutically acceptable carriers for the compositions of this invention include, but are not limited to, sterile pyrogen-free water and sterile pyrogen-free physiological saline solution.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention is designed to address a physiological injury (incurred by any means) and the induced hypercytokinemia. This is accomplished by treating the acute condition with a mast cell stabilizing compound that reduces the release of mediators from mast cells. These compounds may also be effective at reducing the release of mediators from other cell types. The net effect is to reduce an overly robust reaction of the innate immune system, allowing the adaptive immune system to address the initial problem leading to hypercytokinemia. These compounds may also be combined with a disease specific-compound. The disease specific compound targets the initial injury, but the injury may still have induced or continue to induce a strong cytokine response. The mast cell stabilizing compound reduces the released mediators, reducing hypercytokinemia. A reduction in the acute inflammatory response prevents additional damage produced by out of control inflammation. A combined treatment approach is much more efficacious than a single treatment because it addresses both the harmful injury (e.g., infection) and the even more deleterious cytokine response.

While some mast cell stabilizing compounds have been used in the past as general anti-inflammatory agents, the present invention is distinct from prior uses because it involves treating acute inflammatory conditions as opposed to chronic conditions (e.g., SIRS vs. asthma). In addition, the present invention involves treating symptoms caused by infectious agents such as viruses as opposed to allergic responses to seasonal allergens.

One of the most common conditions that can induce hypercytokinemia is influenza infection. Flu has a massive mortality and cost impact upon the world each year, causing over 30,000 deaths a year on average in the US. While there are vaccines for seasonal flu available, they have limitations in that their effectiveness depends on choosing the correct strains long before the flu season has arrived to enable time for manufacturing. Available antiviral therapies are also limited in their effectiveness, because the virus is able to mutate and become resistant to all currently known antivirals. Even if the virus infecting a patient is sensitive to the antiviral used, inhibition of viral spread does not treat a major health risk of influenza; the induced hypercytokinemia.

Mast cells are the resident sentinels that detect and react to an initial infection by influenza virus. Viral recognition by mast cells is accomplished by pattern recognition receptors and results in rapid degranulation, releasing a plethora of cytokines (Graham et al., *J. Immunol.* 190: 4676 (2013)). This release of mediators calls in the first responders of the immune system, including T cells, to attack the infection. Mast cells continue to release cytokines which spread systemically and continue to recruit more immune cells to the infection. These attracted cells also release cytokines to ramp up the immune response. The result can be a self-reinforcing loop that escalates the response out of proportion to the infection. The acute symptoms that are felt in flu are caused by the mediators, not the damage caused by the virus. If left unchecked, this inflammatory response causes tissue damage in the lungs and reduces lung function, while at the same time providing an ideal environment for bacterial growth that results in pneumonia. If left unchecked, the inflammatory response in the lungs can lead to acute respiratory distress syndrome (ARDS) and death.

Treating a patient with antivirals will not stop this self-reinforcing cycle. In fact, by the time a patient is experiencing symptoms, it is at least 48 hours into an infection. Influenza viral budding begins 6 hours after a cell in infected and continues for days. By the time the infection is detected and antiviral treatment has begun, there is already a high viral load and a robust immune response: the patient is already far down the road leading to cytokine storm. Thus, stopping the virus alone at this stage is not enough to treat the physiological condition of influenza-infected patients.

Thus, one aspect of the invention relates to a method of treating, ameliorating, or preventing hypercytokinemia in a subject in need thereof, comprising administering to the subject a therapeutically effective or prevention effective amount of a mast cell stabilizing compound, thereby treating, ameliorating, or preventing the hypercytokinemia. In some embodiments, the hypercytokinemia is due to a disease, disorder, or condition in the subject. In certain embodiments, the disease, disorder, or condition is not asthma, conjunctivitis, or mastocytosis. In some embodiments, the disease, disorder, or condition is a viral infection, e.g., a respiratory virus infection, e.g., an influenza virus infection. In some embodiments, the disease, disorder, or condition is not influenza infection.

Another aspect of the invention relates to a method of treating, ameliorating, or preventing a disorder associated with hypercytokinemia in a subject in need thereof, comprising administering to the subject a therapeutically effective or prevention effective amount of a mast cell stabilizing compound, thereby treating, ameliorating, or preventing the disorder.

Examples of clinical diagnoses that are associated with acute hypercytokinemia include, without limitation, viral infections such as influenza, influenza-like illness, systemic inflammatory response syndrome (from infectious or non-infectious causes), or sepsis.

In some embodiments, the methods are carried out on subjects that have been diagnosed with hypercytokinemia. In other embodiments, the methods are carried out on subjects that have not been diagnosed with hypercytokinemia but have been diagnosed with or are suspected of having a disease, disorder or condition associated with hypercytokinemia and for which the present methods are expected to be beneficial. As can be seen by this list of clinical diagnoses, a documented elevation of cytokines is not needed to identify patients that would benefit from this treatment. In fact, it is understood by those of skill in the art that the detection of increased systemic levels of cytokines is not always found in patients in which a cytokine storm is causing harmful effects. The local concentration of cytokines, particularly in vital organs, more specifically in the lungs, is of greater importance than the level of cytokines found in circulating plasma. Thus, from a practical perspective, relying on clinical diagnoses such as those listed above which do not measure cytokines but rather focus on symptoms or known causes of increased cytokine levels (like a positive influenza test) are more effective in identifying patients that would benefit from the present invention.

Another aspect of the invention relates to a method of treating, ameliorating, or preventing a viral infection associated with hypercytokinemia in a subject in need thereof, comprising administering to the subject a therapeutically effective or prevention effective amount of a mast cell stabilizing compound, thereby treating, ameliorating, or preventing the viral infection. In some embodiments, the viral infection is a respiratory virus infection, e.g., an influenza virus infection.

In general, a primary viral infection or reactivated latent virus induces a robust cytokine response in patients. This is particularly dangerous in respiratory viruses, but others can also induce dangerous levels of cytokines. In these cases, reducing the magnitude of the hypercytokinemia is beneficial, regardless of which virus causes the response. Even in cases where the symptoms are not life-threatening, the elevation of cytokines causes symptoms and these can be ameliorated by treatment with a mast cell stabilizing compound. Examples of viruses where this treatment method may be beneficial include, but are not limited to, influenza, parainfluenza, norovirus, HIV, parvovirus, sindbis virus, dengue virus, adenovirus, Epstein-Barr virus (EBV), respiratory syncytial virus (RSV), vaccinia virus, metapneumovirus, rhinovirus, cytomegalovirus (CMV), hepatitis viruses (all types), herpes simplex virus (all types), papillomavirus, SARS coronavirus, MERS coronavirus, west Nile virus, yellow fever virus and others. In some embodiments, the virus is not influenza.

A further aspect of the invention relates to a method of treating, ameliorating, or preventing a fever in a subject in need thereof, comprising administering to the subject a therapeutically effective or prevention effective amount of a mast cell stabilizing compound, thereby treating, ameliorating, or preventing the fever. In some embodiments, the fever is associated with a respiratory virus infection, e.g., an influenza virus infection. In some embodiments, the fever is associated with a viral infection or other disorder associated with hypercytokinemia. In some embodiments, the antipyretic effect of the mast cell stabilizing compound results in a decrease in body temperature of at least 1° C., e.g., at 2° C., 3° C., 4° C., 5° C., or more.

In some embodiments, the methods of the invention further comprise administering to the subject an additional therapeutic agent for the disease, disorder, or condition. In some embodiments, the additional therapeutic agent is an antiviral agent, e.g., an anti-influenza agent. Examples of anti-influenza agents include, without limitation, rimantadine, amantadine, oseltamivir (TAMIFLU®), laninamivir (INAVIR®), zanamivir (RELENZA®), peramivir (RAPIVAB®), tamiphosphor, favipiravir, VX-787, AL794, S-033188, AB103, TCAD Combo, Avi-7100, flufivirtide-3, fluconazole (FLUCIDE®), ribavirin (Virazole), endonuclease inhibitors, matrix M1 inhibitors, antibodies to viral proteins, Vis-410, nitazoxanide, NT-300, fludase, alferon, PUR003, EV-077, surfaxin, and homspera. In one embodiment, the anti-influenza agent is oseltamivir. Oseltamivir treatment for infected patients is dosed at 75 mg twice a day for 5 days. This provides a therapeutic dose systemically for a duration deemed appropriate for most cases of influenza A and B. In some embodiments, the additional therapeutic agent is an antipyretic agent, such as ibuprofen, naproxen, ketoprofen, nimesulide, aspirin, and other non-steroidal antiinflammatory drugs, and acetaminophen. In some embodiments, the additional therapeutic drug is an agent used to treat SIRS or sepsis, e.g., anti-anaphylaxis agents such as epinephrine, steroids, and diphenhydramine, or antioxidants such as selenium, glutamine, vitamin E, and eicosapentaenoic acid.

The mast cell stabilizing compound may be any mast cell stabilizing compound known in the art. Examples of mast cell stabilizing compounds include, without limitation, ketotifen, norketotifen, cromolyn, nedocromil, quercetin, pemirolast, olopatadine, ebastine and carebastine. In some embodiments of the methods of the invention, the mast cell stabilizing compound is ketotifen or a pharmaceutically acceptable salt thereof. In some embodiments of the methods of the invention, the mast cell stabilizing compound is norketotifen or a pharmaceutically acceptable salt thereof. In some embodiments, the mast cell stabilizing compound is a combination of ketotifen or a pharmaceutically acceptable salt thereof and norketotifen or a pharmaceutically acceptable salt thereof.

The mast cell stabilizing compound and the additional therapeutic agent may be administered to the subject in the same composition or in separate compositions, e.g., administered concurrently. The additional therapeutic agent can be delivered to the subject on a different schedule or by a different route as compared to the mast cell stabilizing compound. The additional therapeutic agent can be any agent that provides a benefit to the subject.

The methods of the present invention may also be combined with physical treatments that are known in the art to be effective for treating a disease, disorder, or condition. Physical treatments may include, without limitation, surgery (e.g., removal of tissue), transplantation of bone marrow or solid organs, plasmapheresis, modulation (increase or decrease) of the temperature of a subject or a tissue or organ in the subject, or any combination thereof.

The compounds of the invention may be administered to the subject as needed to treat a disease, disorder, or condition. The compound can be administered continuously or intermittently. In one embodiment, the compound is administered to the subject more than once a day or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

An examination of peripheral cytokine levels in infected patients shows that elevated circulating levels of cytokines, especially IP10 and IL-6, are present within hours of infection with a peak between day 2 and 4 post-infection. Symptoms generally appear around 2 days post-infection. Cytokine levels rise to much higher levels in patients with more severe symptoms and remain elevated. Due to the variability of severity and course of infection from person to person, combination therapy may be administered initially for 5 days and then continued until symptoms have significantly resolved towards baseline.

The compounds of the invention can be delivered to the subject by any suitable route, e.g., oral, rectal, buccal (e.g., sub-lingual), vaginal, parenteral (e.g., subcutaneous, intramuscular, intradermal, or intravenous), topical (i.e., both skin and mucosal surfaces, including airway surfaces), nasal and/or oral inhalation, and transdermal administration.

Where the antiviral agent is administered by inhalation (e.g., zanamivir), the mast cell stabilizing compound and the antiviral agent may be combined in an inhaler for simultaneous delivery. The advantage of this approach is to deliver both active compounds directly to the site of infection, potentially decreasing the time needed to reach therapeutic levels in infected cells and thereby increasing effectiveness. An additional advantage of using a mast cell stabilizing compound (e.g., ketotifen with an inhaled antiviral) is its effectiveness for treating asthma. One safety issue with zanamivir is the appearance of adverse events in patients with asthma and chronic obstructive pulmonary disorder. It is possible that the anti-inflammatory properties of mast cell stabilizing compounds such as ketotifen may reduce these events and increase the population in which an inhaled antiviral can be utilized.

Some new antiviral therapies may be developed that require only a single dose. Two examples under development are an anti-flu monoclonal antibody or a cap-dependent endonuclease inhibitor. In conjunction with such treatments, a mast cell stabilizing compound may be added to the treatment and be delivered over several days, likely more than 3 days, in order to reduce the impact of hypercytokinemia. A time-release microsphere approach could also be used to simultaneously deliver the mast cell stabilizing compound and ensure that it is present for an extended time, even with only one dose. Shiny et al. (*Int. J. Pharm. Investig.* 3(3): 119 (2013)) is an example of an approach for up to 30-day continuous delivery.

Some viral illnesses can cause severe symptoms requiring hospitalization. For patients in hospital it may be advantageous to provide therapies by intravenous means. For this purpose, an antiviral and a mast cell stabilizing compound can be given through an IV, providing dosing of both medications for the required time period. In this way, seriously ill patients that are unable to swallow medication will be able to be treated with this combination of medication.

The compounds are delivered to the subject at a dose that is effective to treat the disorder. The effective dosage will depend on many factors including the gender, age, weight, and general physical condition of the subject, the severity of the disorder, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* ($21^{st}$ ed. 2005)). In one embodiment, the mast cell stabilizing compound is administered at a dose of about 0.001 to about 500 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10 20, 30, 40, 50, 60, 70, 80, 90, 100, 200, 300, 400, or 500 mg/kg or any range therein. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. For ketotifen the dosing range may be from about 0.001 mg/kg to about 40 mg/kg, e.g., from about 0.01 mg/kg to about 20 mg/kg, e.g., about 0.001, 0.005, 0.01, 0.05, 0.1, 0.5, 1, 2, 3, 4, 5, 6, 7, 8, 9, 10 15, 20, 25, 30, 35, or 40 mg/kg or any range therein. For norketotifen the dosing range may be from about 0.001 mg/kg to about 500 mg/kg, e.g., from about 0.01 mg/kg to about 200 mg/kg e.g., about 0.001, 0.005, 0.01, 0.05, 0.1, 0.5, 1, 2, 3, 4, 5, 6, 7, 8, 9, 10 15, 20, 25, 30, 35, 40, 45, 50, 55, 60, 65, 70, 75, 80, 85, 90, 95, or 100, 150, 200, 250, 300, 350, 400, 450, or 500 mg/kg or any range therein. The present invention encompasses every sub-range within the cited ranges and amounts. These doses may be administered once per day or more than once per day, e.g., 2, 3, or 4 times per day.

Because symptoms of influenza do not generally appear until one or two days into the infection, it is desirable that systemic therapeutic levels of the mast cell stabilizing compound and the additional therapeutic agent be obtained quickly to prevent both viral spread and the accumulation of higher level of cytokines. In order to accomplish this in a way that will provide easy patient compliance, a time release form of administration may be advantageous. FIG. 1 illustrates serum levels predicted for 4 mg per day ketotifen in several different dosing regimens based on published pharmacokinetic data.

Twice daily dosing at 2 mg per dose is the current approach used for mast cell disorders. It takes at least 2.5 days to approach a steady state level near 2 ng/ml. If the 4 mg/day dosing is taken in one dose, it surpasses the steady state level rapidly, but each day the overall level drops significantly and falls below 2 ng/ml. If a time release approach is used with the first dose doubled to 8 mg, the 2 ng/ml level is achieved quickly, the overall level does not go too high and a consistent dose above 2 ng/ml is maintained. Thus, the use of a time release approach, optionally with an increased initial dose, allows for a rapid increase of systemic drug levels that are maintained throughout the treatment.

One property of many viruses, including influenza, is that they cause a great deal of nasal inflammation and secretions. It may be advantageous to deliver this combination of an antiviral agent and mast cell stabilizing compound using an intranasal route (e.g., by nasal instillation and/or nasal inhalation), providing the mast cell stabilizing compound directly to the sinus cavity. Sinus cavities are rich in vasculature, enabling many drugs to be efficiently absorbed systemically using this approach. In fact, ketotifen has been shown to be more bioavailable using intranasal delivery in rabbits than any other route. An additional benefit of a mast cell stabilizer like ketotifen is its antihistamine properties, allowing for a rapid and efficient reduction in severe nasal symptoms.

Some medications are delivered subcutaneously or intramuscularly to ensure the availability of compounds that are not readily absorbed by other administration routes. This method also has the advantage of speed and being practical in hospitals, physician's offices, pharmacies and the home. There are many auto injector systems available that would facilitate self-injection of therapeutic doses of the combination of the invention. In this case the compounds may be mixed in a single chamber if they are compatible, or a dual chamber system may be employed to keep the antiviral and mast cell stabilizing compound in separate compartments until dosing. As it is likely that the dosing schedule will be several days, a system that allows for multiple dosing from a single device (or "pen") would increase convenience and compliance with the needed injection schedule.

For some patients (including children), swallowing tablets or pills is difficult or impossible. In these cases, it may be advantageous to deliver the combination of the invention in an oral liquid formulation. This formulation may deliver the drug combination in a time release mechanism or any other desired delivery profile. This may also be accomplished using a suppository for intra-rectal delivery.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has hypercytokinemia or a disorder associated with hypercytokinemia, e.g., viral infections such as influenza, influenza-like illness, systemic inflammatory response syndrome, or sepsis, or a fever. In other embodiments, the subject is a human subject at risk for developing hypercytokinemia or a disorder associated with hypercytokinemia, e.g., a subject that has been exposed to a virus or is living or working with a subject known to have a viral infection. When a virus like influenza infects an individual, a detectable increase in systemic cytokines starts within hours of infection. While the associated local inflammation may serve to restrict spreading of the virus, in most cases the systemic increases in cytokines does little to prevent the spread of infection and likely slows down the clearance of virus by the adaptive immune system. In addition, the accumulated fluids from inflammation aid in the spread of the virus through sneezing and coughing. The microdroplets produced enable viral particles to remain viable for extended times in an aerosol, allowing it to spread more effectively. The methods of the invention may be used prophylactically to reduce symptoms in anyone infected and reduce the spread of virus. In other embodiments, the subject used in the methods of the invention is an animal model of hypercytokinemia or a disorder associated with hypercytokinemia.

The subject can be a subject "in need of" the methods of the present invention, e.g., in need of the therapeutic and/or prophylactic effects of the inventive methods.

In some embodiments, the subject is one that is in a higher risk population for the viral infection, e.g., influenza infection. These would include, but are not limited to, the elderly, the very young, pregnant women, immunocompromised patients, and ethnic groups shown to be at higher risk (for example American Eskimo, Native American). In addition, very virulent strains of influenza have induced more severe disease in healthy individuals between the ages of 20 and 50 (the pandemic strain from 2009 being the most recent example), and this regime is likely to be more effective in this group for a virulent strain.

A further aspect of the invention relates to a pharmaceutical composition comprising norketotifen and a pharmaceutically acceptable carrier. The pharmaceutical composition may further comprise an additional therapeutic agent, e.g., an antiviral agent, e.g., an anti-influenza agent, e.g., oseltamivir.

Another aspect of the invention relates to a pharmaceutical composition comprising ketotifen, an additional therapeutic agent, and a pharmaceutically acceptable carrier. In some embodiments, the additional therapeutic agent is an antiviral agent, e.g., an anti-influenza agent, e.g., oseltamivir.

An additional aspect of the invention relates to a dosage form comprising the pharmaceutical composition of the invention. The dosage form may be any dosage form known in the art that is suitable for the methods of the present invention. The dosage form may be, without limitation, a solid or liquid oral dosage form, a dosage form for nasal and/or oral inhalation, a dosage form for intravenous administration, a dosage form for transdermal or mucosal administration (e.g., a patch), a dosage form for injection (e.g., subcutaneous or intramuscular), a dosage form for implantation (e.g., a dissolvable formulation or a device such as a pump), or a dosage form for ocular administration.

The compounds of this invention (e.g., mast cell stabilizing compounds such as ketotifen and norketotifen) include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

Compounds of the invention include those having quaternization of any basic nitrogen-containing group therein.

The discussion herein is, for simplicity, provided without reference to stereoisomerism. Those skilled in the art will appreciate that the compounds of the invention can contain one or more asymmetric centers and thus occur as racemates and racemic mixtures, single optical isomers, individual diastereomers, and diastereomeric mixtures. All such isomeric forms of these compounds are expressly included in the present invention.

Similarly, compounds of the invention containing a double bond can exist in the form of geometric isomers, which can be readily separated and recovered by conventional procedures. Such isomeric forms are included in the scope of this invention.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

The compounds of the invention described above can be formulated for administration in a pharmaceutical carrier in accordance with known techniques. See, e.g., Remington, *The Science And Practice of Pharmacy* ($21^{st}$ ed. 2005). In the manufacture of a pharmaceutical composition according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), nasal and/or oral inhalation, and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a multiparticulate, powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

The term "tablet" as used herein includes, but is not limited to, immediate release (IR) tablets, sustained release (SR) tablets, extended release (ER) tablets, matrix tablets, multilayer tablets, multilayer matrix tablets, delayed release tablets and pulsed release tablets, any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms that may be useful in the practice of the invention include those selected from the group consisting of IR tablets, SR tablets, ER tablets, coated IR tablets, coated SR tablets, coated ER tablets, matrix tablets, coated matrix tablets, multilayer tablets, coated multilayer tablets, multilayer matrix tablets and coated multilayer matrix tablets. In some embodiments, a tablet dosage form is an enteric-coated tablet dosage form. In some embodiments, a tablet dosage form is an enteric-coated extended release tablet dosage form.

The term "capsule" as used herein includes, but is not limited to, IR capsules, SR capsules, ER capsules, coated IR capsules, coated SR capsules, and ER capsules, including delayed release capsules. Capsules may be filled with powders, granules, multiparticulates, tablets, semi-solids, or liquids. In some embodiments, a capsule dosage form is an enteric-coated capsule dosage form. In some embodiments, a capsule dosage form is an enteric-coated extended release capsule dosage form. Capsules may be made of hard gelatin, soft gelatin, starch, cellulose polymers, or other materials as known to the art.

The term "multiparticulate" as used herein means a plurality of discrete particles, microparticles, nanoparticles, pellets, mini-tablets and mixtures or combinations thereof. If the oral form is a multiparticulate capsule, hard or soft gelatin capsules or capsules of other materials can suitably be used to contain the multiparticulate. In some embodiments, a sachet can suitably be used to contain the multiparticulate. In some embodiments, the multiparticulate may be coated with a layer containing rate controlling polymer material. In some embodiments, a multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

In some embodiments, the multiparticulate and one or more auxiliary excipient materials can be compressed into tablet form such as a multilayer tablet. In some embodiments, a multilayer tablet may comprise two layers containing the same or different levels of the same active ingredient having the same or different release characteristics. In some embodiments, a multilayer tablet may contain different active ingredients in each layer. Such a tablet, either single layered or multilayered, can optionally be coated with a controlled release polymer so as to provide additional controlled release properties. In some embodiments, a multiparticulate dosage form comprises a capsule containing delayed release rapid onset minitablets. In some embodiments, a multiparticulate dosage form comprises a delayed release capsule comprising instant release minitablets. In some embodiments, a multiparticulate dosage form comprises a capsule comprising delayed release granules. In some embodiments, a multiparticulate dosage form comprises a delayed release capsule comprising instant release granules.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 0.001 mg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal formulations containing the compound disclosed herein, can be lyophilized to produce a lyophilizate which can be reconstituted with a pharmaceutically acceptable carrier, such as water, to regenerate a liposomal suspension.

In certain embodiments, the dosage form is an extended release dosage form. The dosage form may have a half-life of at least 24 hours. In some embodiments, the extended release dosage form will provide a slower release of the drug over a 24-hour time period such that a consistent, tight range of the drug is available systemically for 24 hours. In certain embodiments, as shown in the example in FIG. 1, the serum level of the compound is kept above 2 ng/mL throughout the treatment period, but at the same time does not rise above 2.5 ng/mL. The dosage form may comprise and/or be coated with a rate controlling polymer material, e.g., hydroxypropyl methylcellulose, a polymer of acrylic or methacrylic acid or their respective esters, or copolymers of acrylic or methacrylic acid or their respective esters.

In any of the above-mentioned embodiments, a controlled release coating (e.g., an enteric coating) may be applied to the final dosage form (capsule, tablet, multilayer tablet, etc.). The controlled release coating may typically comprise a rate controlling polymer material as defined above. The dissolution characteristics of such a coating material may be pH dependent or independent of pH.

The term "rate controlling polymer material" as used herein includes hydrophilic polymers, hydrophobic polymers and mixtures of hydrophilic and/or hydrophobic polymers that are capable of controlling or retarding the release of the compound from a dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly(alkylmethacrylate) and poly (vinyl acetate). Other suitable hydrophobic polymers include polymers and/or copolymers derived from acrylic or methacrylic acid and their respective esters, zein, waxes, shellac and hydrogenated vegetable oils. Particularly useful in the practice of the present invention are poly acrylic acid, poly acrylate, poly methacrylic acid and poly methacrylate polymers. Some of these polymers (e.g., poly methacrylate polymers) can be used as delayed release polymers to control the site where the drug is released.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A pharmaceutical composition for treating influenza, comprising norketotifen, an anti-influenza agent, and a pharmaceutically acceptable carrier.

2. The pharmaceutical composition of claim 1, wherein the anti-influenza agent is oseltamivir.

3. A dosage form comprising the pharmaceutical composition of claim 1.

4. The dosage form of claim 3, wherein the dosage form is an extended release dosage form.

5. The dosage form of claim 3, which is a solid or liquid oral dosage form.

6. The dosage form of claim 3, which is a dosage form for nasal and/or oral inhalation.

7. The dosage form of claim 3, which is a dosage form for intravenous administration.

8. The dosage form of claim 3, which is a dosage form for transdermal or mucosal administration.

9. The dosage form of claim 3, which is a dosage form for injection.

10. The dosage form of claim 3, which is a dosage form for implantation.

11. The dosage form of claim 3, which is a dosage form for ocular administration.

* * * * *

UNITED STATES PATENT AND TRADEMARK OFFICE
CERTIFICATE OF CORRECTION

PATENT NO. : 10,160,796 B2
APPLICATION NO. : 15/816461
DATED : December 25, 2018
INVENTOR(S) : Hyde-DeRuyscher et al.

Page 1 of 1

It is certified that error appears in the above-identified patent and that said Letters Patent is hereby corrected as shown below:

On the Title Page

Item (56) References Cited, FOREIGN PATENT DOCUMENTS:
Please correct "WO 2016130958 A1 8/2016" to read -- WO 2016130968 A1 8/2016 --

In the Specification

Column 15, Line 53: Please correct "(FR)" to read -- (ER) --

Signed and Sealed this
Thirtieth Day of April, 2019

Andrei Iancu
*Director of the United States Patent and Trademark Office*